United States Patent [19]
Olsen

[11] Patent Number: 5,460,815
[45] Date of Patent: Oct. 24, 1995

[54] FELINE INFECTIOUS PERITONITIS VACCINE AND METHOD OF PREPARATION

[75] Inventor: Richard G. Olsen, London, Ohio

[73] Assignee: Parhelion Corporation, Columbus, Ohio

[21] Appl. No.: 206,268

[22] Filed: Mar. 7, 1994

Related U.S. Application Data

[63] Continuation of Ser. No. 838,132, Feb. 18, 1992, abandoned.

[51] Int. Cl.[6] .................. A61K 39/215; C12N 7/00; C12N 5/06; C12N 5/10
[52] U.S. Cl. .................. 424/221; 435/235.1; 435/240.2
[58] Field of Search .................. 424/221.1; 435/240.2, 435/240.3, 240.31, 235.1

[56] References Cited

U.S. PATENT DOCUMENTS

| | | | |
|---|---|---|---|
| 4,195,130 | 3/1980 | Hoshino | 435/235.1 |
| 4,287,178 | 9/1981 | Bittle | 424/229.1 |
| 4,293,653 | 10/1981 | Horzinek | 435/237 |
| 4,303,644 | 12/1981 | Davis | 424/202.1 |
| 4,434,157 | 2/1984 | Olsen | 424/207.1 |
| 4,571,386 | 2/1986 | Fishman | 435/235.1 |
| 5,043,157 | 8/1991 | Baldwin | 424/221.1 |

FOREIGN PATENT DOCUMENTS

| | | |
|---|---|---|
| 0264979 | 4/1988 | European Pat. Off. ........ C12N 15/00 |
| 0376744 | 7/1990 | European Pat. Off. ........ C12N 15/50 |
| 0411684A2 | 2/1991 | European Pat. Off. . |

OTHER PUBLICATIONS

Harry Vennema et al., "Primary Structure of the Membrane and Nucleocapsid Protein Genes of Feline Infectious Peritonitis Virus and Immunogenicity of Recombinant . . . ", *Virology*, Dec. 1990, pp. 1–9.

Harry Vennema, "The Proteins of Feline Infectious Peritonitis Coronavirus: Their Biosynthesis and Involvement in Pathogenesis", Dec. 1, 1961, pp. 5–139.

Gerber, J. D. et al. (90) Vaccine 8: 536–542.

*Primary Examiner*—Mary E. Mosher
*Attorney, Agent, or Firm*—Oblon, Spivak, McClelland, Maier, & Neustadt

[57] ABSTRACT

One aspect of the present invention comprises a vaccine for the prevention of disease caused by feline infectious peritonitis virus (FIPV). Such vaccine comprises FIP viral precursor immunogens derived from in vitro produced cells persistently infected with FIPV. Preferred in the production of viral immunogens forming the vaccine of the present invention is the Crandall Feline Kidney (CrFK) cell line. Thus, a second aspect of the invention comprises FIP-infected Crandall Feline Kidney cell line, deposited at the American Type Culture Collection (ATCC), Rockville, MD, on Sep. 23, 1992, and granted Accession No. CRL11137. A third aspect of the invention relates to a method of producing FIP viral precursor immunogens, which comprises culturing in vitro FIP-persistent infected cells in a serum-containing growth medium, subsequently transferring and maintaining said cultured cells in a serum-free medium under conditions and for a time adequate to accumulate FIP viral precursor immunogens shed from said cells, and then separating the cells from the supernatant containing the vital precursor immunogens. The supernatant containing the FIP viral precursor immunogens is blended with a pharmaceutically-acceptable adjuvant in order to form the FIP vaccine disclosed herein.

13 Claims, No Drawings

FELINE INFECTIOUS PERITONITIS VACCINE AND METHOD OF PREPARATION

This is a continuation of application Ser. No. 07/838,132 filed Feb. 18, 1992 now abandoned.

BACKGROUND OF THE INVENTION

Feline infectious peritonitis (FIP) is a sporadic disease occurring unpredictably in domestic and wild Felidae. While FIP is primarily a disease of domestic cats, it has been diagnosed in lions, mountain lions, leopards, cheetahs, and the jaguar. Smaller wild cats that have been afflicted with FIP include the lynx and caracal, sand cat, and pallas cat. In domestic cats, the disease occurs predominantly in young animals, although cats of all ages are susceptible. A peak incidence occurs between 6 and 12 months of age. A decline in incidence is noted from 5 to 13 years of age, followed by an increased incidence in cats 14 to 15 years old. There is no significant sex predisposition. FIP occurs more frequently in purebred cats, presumably because these cats are kept more commonly in catteries or multiple cat households. The disease is world-wide in distribution.

FIP is caused by a type of coronavirus. Coronaviruses are pleomorphic, enveloped particles that average 100 nm in diameter and contain a single strand of RNA. Characteristic petal-shaped projections called peplomers pronude from the viral surface. In many species of animals, coronaviruses have a relatively restricted organ tropism, infecting the respiratory and/or gastrointestinal systems. Following oral infection, the viruses have an affinity for the mature apical columnar epithelium of the villi in the duodenum, jejunum, and ileum.

The coronaviruses that infect cats have been divided into those that cause FIP (FIPVs) and those that induce subclinical to severe enteritis (the feline enteric coronaviruses, or FECVs). The FIPVs differ from the FECVs in theft ability to escape from the gastrointestinal tract and spread to replication sites in distant tissues. FIPVs and FECVs may represent pathogenetic variants of a single coronavirus type. Alternatively, FIPVs may arise periodically as mutants of FECV strains.

FIPV, transmissible gastroenteritis virus (TGEV) of swine, canine coronavirus (CCV), and human respiratory tract coronaviruses of the 229E group comprise an antigenic cluster of closely related viruses within the Coronaviridae group. The major structural polypeptides of FIPV, TGEV, and CCV are so similar antigenically that some consider these three viruses as host range mutants rather than individual viral species.

The name, feline infectious peritonitis, refers to the principal form of the disease, an inflammatory condition of the visceral serosa and omentum. A reported second form of FIP is characterized by granulomatous involvement of parenchymatous organs such as the kidneys, mesenteric lymph nodes, liver, pancreas, central nervous system (CNS) and spine, and the uveal tract of the eye. The granulomatous form of FIP is called "dry" or "noneffusive" because there is no inflammatory exudation into the body cavities. Classical FIP, which comprises about three-fourths of the cases, is termed "wet" or "effusive." A third form of FIP combines characteristics of both the effusive and noneffusive varieties.

The clinical course of effusive FIP lasts from 1 to 6 weeks or sometimes longer. The onset of disease is heralded by the appearance of a chronic, fluctuating fever. Associated with the fever there is usually a progressive decline in weight, activity, and appetite. Terminally, the cats go into shock and die. Peritonitis is seen in over 90% of the cats with effusive FIP and pleuritis in around 40% of the cases. Involvement of other organs, such as the eyes and CNS, is clinically apparent in only 10% of the cats with effusive disease, although a somewhat higher proportion may have clinically silent lesions in these and other non-serosal sites.

Cats with noneffusive FIP are ordinarily ill for 1 to 12 weeks or longer. As with the effusive form, a chronic fluctuating fever accompanies the disease. There also is a progressive decline in general body condition and appetite. Added to these features, however, are signs referable to specific organ systems. Peritoneal cavity lesions are found in 50% of cats with noneffusive FIP and pleural cavity lesions in 10%. Noneffusive FIP differs from the effusive form in that there is a high incidence of ocular or CNS involvement. Approximately one-third of cats with noneffusive FIP demonstrate signs referable to the CNS, and a similar number have clinically-apparent ocular disease.

The precise routes by which FIPV enters the body are not known. FIPV is a heat-labile virus, being inactivated at room temperature within 24 to 48 hours. It is unlikely that cats with FIP are the only source of FIPV in nature. Similarly, contaminated fomites are an unlikely source of infection, given the short stability of FIPV outside the host. In most cases, transmission of virus probably occurs via the feces and, less commonly, the urine or oronasal secretions of asymptomatic carriers. To explain the sporadic and random incidence of the disease, carder cats would have to shed the virus either intermittently or at exceedingly low levels.

Queens that are asymptomatically infected with FIPV may infect their offspring in-utero or in the neonatal period. Kittens infected in-utero may be born sick or may show no signs of disease. However, some asymptomatic infected kittens may develop FIP at a later time if their immune responsiveness becomes impaired.

Concurrent infection with feline leukemia virus (FeLV) has been reported in cats infected with FIPV. The mechanism by which FeLV infection potentiates the incidence of FIPV is not specifically known, although controlled observations reported in the literature have led to the assumption that FeLV infection in some way interferes with established FIPV immunity. The mechanism of this interference has been speculated to involve any number of generalized immunosuppressive effects that have been described in connection with persistent FeLV infection, which dispose cats to intercurrent or opportunistic infections.

Specific pathogen-free (SPF) kittens that are exposed to FIPV by oral or intratracheal instillation react serologically in several ways. Some kittens do not develop any signs of infection after prolonged exposure, and they remain antibody-negative. Kittens which are infected but do not develop signs of illness demonstrate a plateau-shaped antibody response, while kittens that develop FIP demonstrate a progressive antibody titer rise. In both groups of infected kittens, the presence of virus-neutralizing antibodies tends to correlate with immunofluorescent antibody (IFA) titers. Sometimes, however, an infected cat will develop only virus-neutralizing antibodies, and IFA tilers will be negligible. Difficulty is encountered in the interpretation of serologic responses due to antigenic similarity between FIPV and the non-FIP-inducing coronaviruses (FECV), and the ubiquitousness of FECV infection in nature. About 25% of free-roaming cats have been or remain infected with FECV, with infections especially prevalent in catteries and multiple cat households. Infection with FECV results in the production of coronaviral antibody that is, at present, serologically indistinguishable from that induced by infection with FIPV, CCV, or TGEV.

Antibody formed as a result of FECV infection does not protect the cat from later challenge with a virulent strain of FIPV. In fact, this antibody sensitizes the cat to later challenge, accelerating the disease process induced by the virulent FIPV.

Initial attempts to immunize cats with TGEV of swine to provide protection against FIP have proven unsuccessful, although immunization of piglets with FIPV is known to invoke antibody production against TGEV. To date, immunization with killed FIPV also has proven uniformly unsuccessful. The immunity derived from autologous killed vaccines almost always renders cats more susceptible to challenge with the virulent living virus, and the disease that results usually is more severe and fulminating. Vaccination with attenuated FIPV also has proven unsuccessful as evidenced by a lack of such products commercially. In this regard, reference is made to Gerber et al, "Protection Against Feline Infectious Peritonitis by Intranasal Inoculation of a Temperature-Sensitive FIPV Vaccine", Vaccine, Vol. 8, pp 536–542 (December 1990); and U.S. Pat. Nos. 4,293,653, 4,303,644, and 4,571,386.

The prognosis for cats with FIP is poor, since there is currently no effective treatment to terminate the viral infection. Some treatment regimens allow short-term remissions in carefully selected patients. The best patients for palliative therapy are those cats with FIP that are not infected with FeLV, are in good physical condition, maintain a good appetite, and have no evidence of severe anemia or neurologic signs. Unfortunately, few cats with FIP are presented early enough in the course of disease to meet these criteria, and most afflicted cats will die within 1 to 16 weeks.

Sources of additional information concerning FIP include Olsen et al., Comparative Pathobiology of Viral Diseases, vol.2, pp.115–136, CRC Press, Inc., Boca Raton, Fla. (1985), and references cited therein; and Norden News, Autumn 1989, pp.15–19, Lincoln, Nebr., the disclosures of which are incorporated expressly herein by reference.

BROAD STATEMENT OF THE INVENTION

One aspect of the present invention comprises a vaccine for the prevention of disease caused by feline infectious peritonitis virus (FIPV). Such vaccine comprises FIP vital precursor immunogens derived from in vitro produced cells persistently infected with FIPV. Preferred in the production of vital immunogens forming the vaccine of the present invention is the Crandall Feline Kidney (CrFK) cell line.

Thus, a second aspect of the invention comprises FIP-infected Crandall Feline Kidney cell line, deposited on Sep. 23, 1992 at the American Type Culture Collection (ATCC), Rockville, Md., granted Accession No. CRL11137.

A third aspect of the invention relates to a method of producing FIP vital precursor immunogens, which comprises culturing in vitro FIP-persistently infected cells in a serum-containing growth medium, subsequently transferring and maintaining said cultured cells in a serum-free medium under conditions and for a time adequate to accumulate FIP viral precursor immunogens shed from said cells, and then separating the cells from the supernatant containing the vital precursor immunogens. The supernatant containing the FIP vital precursor immunogens is blended with a pharmaceutically-acceptable adjuvant in order to form the FIP vaccine disclosed herein.

DETAILED DESCRIPTION OF THE INVENTION

The vaccine of the present invention effectively protects cats against disease associated with FIPV. Furthermore, inoculated cats do not serve as carders of the disease. This protection, coupled with the fact that the vaccine is ostensibly virus-free, underscores obvious and highly significant advantages conveyed by the inventive vaccine. Because the vaccine utilizes neither living nor dead virus, but rather a product of viral-infected cells (i.e., viral precursor immunogens), it is not only extremely effective but essentially risk-free as well.

The inventive FIP vaccine can be combined with vaccines effective against other feline diseases without prejudicing its efficacy. Other vaccines which may be combined with the instant vaccine include, for example, vaccines against feline leukemia virus (FeLV), feline sarcoma virus (FeSV), feline panleukopenia virus (FPV), feline calicivirus (FCV), and feline herpesvirus I (FHV-I), which causes feline viral rhinotracheitis.

The vital precursor immunogens derived from the persistently-infected cells are proteins or protein precursors (i.e., unassembled viral proteins) associated with FIP. With reference to the method of collecting the viral precursor immunogens, the first step requires the selection of a cell line capable of persistent infection with FIPV, but for which FIPV is noncytotoxic. Further, it is desirable not to sacrifice the cell line for the sake of harvesting the viral precursor immunogens. Thus, the cell line of choice should not only be capable of persistent infection with FIP, but should also be amenable to the harvesting of vital precursor immunogens followed by recycle to the process for subsequent rounds of growth and harvesting.

The presently preferred cell line of choice yielding the FIP vaccine disclosed herein comprises Crandall Feline Kidney (CrFK) cells which have been persistently infected with FIPV. The Dahlberg strain of FIPV (ATCC Accession No. VR-867) is used. The persistently infected cell line of the present invention has been assigned ATCC Accession No. CRL11137.

The infected CrFK cells first are placed in a serum-containing growth medium for culture. Such serum-containing growth medium comprises a conventional serum-free growth medium having added thereto an appropriate quantity of animal serum, such as fetal bovine serum. Appropriate serum-free media include McCoy's 5a medium and RPMI 1640 medium (Gibco, Grand Island, N.Y.), and like conventional media. To such serum-free medium are added appropriate quantities of serum and antibiotics in conventional fashion. The cells are cultured in such medium, with additional serum optionally added from time to time, preferably until such cells have reached saturation density in the volume of medium used. Conventional growth conditions are maintained as well known in the art.

The next step of the process comprises transferring the cultured presistently-infected cells to a serum-free growth medium of composition desirably substantially the same as that used in the culturing step, except that no serum is used or added during this subsequent step. The cells placed in the serum-free medium apparently cease their normal growth cycle and virtually all vital production is arrested. As a result of the severe stress to which the cells are subjected in serum-free medium, an abundance of viral precursor immunogens (and possibly additional cell matter) are shed from the cells in substantial quantities.

The supernatant, comprising serum-free medium containing viral precursor immunogens, then is separated from the persistently-infected cells by conventional separation techniques including, for example, centrifugation. The separated cell line can then be recycled to the culturing step of the process, with serum-containing growth medium.

The FIP viral precursor immunogens may be lyophilized or can be converted into a vaccine immediately. If lyophilization is the technique of choice, the viral precursor immunogen powder can be stored in such form or, if preferred, can be resuspended and stored at very low temperatures (e.g., −67.8° to −126.7° C.).

In order to convert the FIP viral precursor immunogens into a vaccine which is effective for the prevention of diseases caused by FIPV, the FIP vital precursor immunogen supernatant, preferably diluted to minimal effective amount, is blended with a pharmaceutically-acceptable adjuvant. The determination of FIP vital precursor immunogens separated from the harvested infected cell lines can be conveniently determined by dot-blot analysis. Thereafter, pharmaceutically-acceptable adjuvants are added in conventional amounts to the HP viral precursor immunogen serum-free medium. Conventional adjuvants include, for example, complete or incomplete Freund's adjuvant, aluminum hydroxide, Quil A, EMA, DDA, TDM-Squalene, lecithin, alum, saponin, and such other adjuvants as are well known to those in the art, and also mixtures thereof.

The vaccine, as prepared or in combination with other feline vaccines or inoculants, can be used to inoculate both domestic and wild Felidae for the prevention of disease associated with FIPV. Viral precursor immunogen units per dosage are administered to these cats by conventional routes of administration, e.g., parenteral inoculation, including subcutaneous and intramuscular vaccination, or oral administration. Parenteral inoculation is the preferred route of administration.

Both kittens and adult cats can be vaccinated with the vaccine and thereby receive full protection from infection. The preferred minimum age of the kitten for inoculation, as with most other vaccines, is at about 8 weeks when the kitten has been weaned and maternal antibody has disappeared. A suggested time range for vaccination, thus, encompasses the period of 6 to 12 weeks of age.

The following example illustrates the manner in which the present invention has been practiced, but should not be construed as limiting. All units herein are in the metric system unless otherwise expressly indicated, and all references cited herein are expressly incorporated by reference.

EXAMPLE

Crandall Feline Kidney (CrFK) cell line was infected with feline infectious peritonitis virus (ATCC-VR-867; Dahlberg strain) diluted 1:100 and incubated 1 hour at 37° C. The cells were incubated at 37° C. until cytopathic effect (CPE) was maximal.

Fresh growth medium (GM), comprising Eagles Minimum Essential Medium (MEM) containing Earles Salts and supplemented with 10% heat-inactivated fetal bovine serum, antibiotic mixture, and 2 mM glutamine, was added to the flask and incubated at 37+ C. The cultures were examined every three days and small islands of cell growth were observed. Fresh GM was added until the cells reached confluency. Cultures then were maintained by the addition of 0.025% trypsin, to remove and dissociate cells from the flask into single cells, and passaged to other flasks. The cells also were grown on cover slips and examined for virus production by indirect immunofluorescent antibody (IIFA) technique with FIP monoclonal antibody as the primary reagent. Cell lines were monitored each passage for virus production and were frozen for storage every five passages.

IIFA was conducted according to the following procedure:

1. Cover slips were sterilized by steam sterilization in glass Petri dishes.
2. CrFK-FIP cells were added to cover slips in GM and incubated until confluent, usually 48 hours.
3. Medium was decanted and cells washed with Dulbecco's calcium-magnesium-free phosphate-buffered saline (CMF-PBS).
4. The dishes were filled with –20° C. acetone and fixed in the freezer for 10 minutes. The acetone was removed, and the cells were air-dried and either used immediately or stored "dry" at –20° C.
5. Cover slips were flooded with FIP monoclonal antibody, diluted 1:1000, and incubated for 30 minutes at 37° C. in a humidified atmosphere.
6. The cells were washed 3 times with CMF-PBS at 5 minutes per wash, dried, and secondary reagent was added.
7. Rabbit anti-mouse IgG conjugated with fluorescein isothiocyanate (FITC) diluted 1:40 comprised the secondary reagent.
8. The secondary reagent was incubated and washed as described in steps 5 and 6.
9. Following the last wash, the cover slips were dipped in distilled water, air-dried, and mounted cell-side-down on a glass microscope slide in a 1:1 mixture of glycerin:CMF-PBS.
10. The cells were examined with an ultraviolet epifluorescent microscope with appropriate exciter and barrier filters.
11. Positive cells were identified by granular apple-green cytoplasmic fluorescence.
12. Noninfected CrFK cells were utilized as controls.

For vaccine production, virus-tested cells were transferred to large plastic T-flasks (75 or 250 mM) in GM and incubated at 37° C. until confluent. The medium was replaced with serum-free GM and incubated at 37° C. for 72 hours. Samples were removed for testing at 24 and 48 hours. At 72 hours, the medium was collected and centrifuged to remove cellular debris. Clarified supernatants were concentrated 10×by dialysis with polyethylene glycol 1000 (Aquacide III, Calbiochem, La Jolla, Calif.) at 4° C. The 10×concentrated supernatant was tested for FIP antigens by dot-blot analysis and frozen at –85° C.

The dot-blot analysis was conducted as follows:

1. 1×and 10×vaccine preparations were tested.
2. 20 microliter samples were pipetted onto strips of nitrocellulose paper (pore size 45 micrometers) and air-dried. The following samples were used:
   - ◇024 hours
   - ◇048 hours
   - ◇072 hours (1×)
   - ◇072 hours (10×)
   - ◇Serum-free MEM only
   - ◇Serum-free MEM from noninfected CrFK cells incubated 72 hours
   - ◇FIP virus (1:50 dilution)
3. Strips were incubated with 5% bovine serum albumin (BSA) at 5 g/80 ml PBS: 20 ml Tween 20 (Sigma Chemical, St. Louis, Mo.) for one hour at 37° C.

4. Strips were incubated in FIP monoclonal antibody solution at 1:200 dilution for one hour at 37° C.

5. Strips were washed 3 times for 10 minutes per wash on an orbital platform in 5% BSA-Tween 20 wash.

6. Strips were incubated with secondary reagent, Staphylococcus protein A conjugated to alkaline phosphatase, diluted 1:500. Strips were placed in BCIP/NBT substrate comprising 1 ml BCIP concentrate, 1 ml NBT concentrate, and 10 ml Tris buffer (Kirke-gaard & Perry Labs, Inc., Gaithersburg, Md.) and the color was developed to desired intensity, usually between 5 and 10 minutes.

7. The reaction was stopped by dipping the strips in distilled water.

8. The strips were air-dried and sealed in tape.

9. The strips were visualized for dark blue/black staining when compared to negative and positive controls.

Inactivation was accomplished by freshly preparing beta-propiolactone at a dilution of 1:100 in distilled deionized water and adding it to a virus suspension at a final concentration of 1:1200, followed by incubation at 37° C. for 2 hours. The inactivated vaccine was tested for infectious virus by titrating inactivated sample on susceptible CrFK cells. Results were considered negative if no viral cytopathology was noted by daily observation of infected cells and appropriate controls.

Twelve SPF cats were used for the immunization and protection studies, in accordance with the following protocol:

◇ Group A: 4 cats, oral administration of vaccine (1.0 ml);

◇ Group B: 4 cats, subcutaneous administration of vaccine (1.0 ml) comprising 1:1 mixture of 10×vaccine concentrate with Septic ISA50 adjuvant (Monatide, Pads, France);

◇ Group C: 4 cats, nonimmunized as controls.

A 3-dose regimen and serum sampling protocol was effected:

◇ Week 0: Condition cats for 2 weeks;

◇ Week 2: Pre-bleed cats for 1.0 ml serum;

◇ Week 3: Pre-bleed cats for 1.0 ml serum and administer first vaccine dose;

◇ Week 4: Trial bleed cats and administer vaccine dose 2;

◇ Week 5: Trial bleed cats and administer vaccine dose 3;

◇ Week 6: Trial bleed cats and administer initial virus challenge;

◇ Week 14: Trial bleed cats and administer second virus challenge;

◇ Week 16: Bleed cats and necropsy.

Summaries of the clinical course and histopathologic findings are set forth in the following tables: t,110 t,111

Animals were observed daily for clinical signs of FIP. As the foregoing data reveal, after the first challenge, three of the four cats in the unvaccinated control group showed clinical signs of FIP. These three cats were euthanized, all in moribund condition, two following the first challenge and the third following the second challenge. Of the vaccinated cats, three of the four cats in Group A and all of the cats in Group B (excepting cat GJ2, which succumbed to anesthesia) remained healthy throughout the study.

In the Group C control cats, lesions typical of FIP were found in a variety of organs. All three of the euthanized cats had effusive peritonitis and multifocal necrotizing to granulomatous lesions in liver, kidney, and lung. Cat GM2 had a peracute histocytic response, while cats GN6 and GR5 evidenced mainly a pyogranulomatous response, more typical of spontaneous FIP. In addition, pyogranulomatous lesions were present in the brains and eyes of the two cats with more prolonged disease, but were absent from the animal which had died acutely. The intestines of all three cats showed mild to severe dilatation of intestinal glands by necrotic debris, leukocytes and mucous, in both the small intestine and colon. In two cats, severe villous atrophy was evident in the ileum; transmural granulomatous enteritis was present in the third cat.

Thus, inoculation of cats with HPV accurately recapitulates the pathological features of severe spontaneous disease, with infected cats developing typical pyogranulomatous lesions. Additionally, this FIP strain induces intestinal lesions which are not dissimilar to coronaviral enteritides in other species, but which have not been associated with spontaneous FIP.

Accordingly, the foregoing data demonstrate that the inventive vaccine provides protection against multiple exposures to a highly virulent FIPV. In addition to being nearly 100% effective, the inventive vaccine possesses significant advantages over traditional modified live vaccine approaches in that there is no risk of shedding infectious virus particles, there is no possibility of reversion to a virulent strain, and the vaccine can be readily mixed with other inactivated vaccines.

I claim:

1. A method of producing a feline infectious peritonitis (FIP) vaccine, which comprises culturing Crandall Feline Kidney cells persistently-infected with Dahlberg strain feline infectious peritonitis virus (FIPV) in a serum-containing growth medium, transferring said persistently-infected cells to a serum-free growth medium, separating said persistently-infected cells from a supernatant containing viral precursor immunogens, inactivating live virus in said supernatant, and formulating a vaccine comprising said viral precursor immunogens.

2. The method of claim 1 wherein said cultured cells are from the cell line designated ATCC Accession No. CRL11137.

3. The method of claim 1 wherein said supernatant is lyophilized and the resulting powder is recovered.

4. The method of claim 1 wherein said immunogens are diluted with a pharmaceutically-acceptable adjuvant.

5. A vaccine composition for the immunization of feline infectious peritonitis-susceptible cats, comprising an immunizing-effective amount of viral precursor immunogens derived from a cell culture supernatant of Crandall Feline Kidney cells persistently infected with Dahlberg strain FIPV and a pharmaceutically-acceptable adjuvant.

6. The FIP vaccine of claim 5 wherein said presistently-infected cells are cultured in a serum-free growth medium.

7. The FIP vaccine of claim 6 wherein said FIP-persistently-infected cells are cultured in serum-containing growth medium and then transferred to said serum-free growth medium.

8. The FIP vaccine of claim 5 wherein said cells are from the cell line designated ATCC Accession No. CRL11137.

9. A method of immunizing a FIP-susceptible cat comprising parenterally inoculating said cat with the vaccine of claim 8.

10. A method of immunizing a FIP-susceptible cat comprising parenterally inoculating said cat with the vaccine of claim 5.

11. The method of claim 10 wherein said pharmaceutically-acceptable adjuvant is selected from the group consisting of complete or incomplete Freund's adjuvant, aluminum hydroxide, Quil A, EMA, DDA, TDM-Squalene, lecithin, alum, saponin, and mixtures thereof.

12. The method of claim 10 wherein said cat is about 6 to 12 weeks of age when inoculated.

13. A Crandall Kidney cell line persistently infected with FIPV, designated ATCC Accession No. CRL11137.

* * * * *